United States Patent [19]
Howell

[11] Patent Number: 5,882,915
[45] Date of Patent: Mar. 16, 1999

[54] VIRIDIOL DEFICIENT MUTANT STRAINS OF THE BIOCONTROL AGENT TRICHODERMA VIRENS, PROCESS OF MAKING AND USING AS BIOCONTROL AGENT

[75] Inventor: Charles R. Howell, Bryan, Tex.

[73] Assignee: The United States of America as represented by the Secretary of Agriculture, Washington, D.C.

[21] Appl. No.: 633,334

[22] Filed: Apr. 17, 1996

[51] Int. Cl.$^6$ .............................. C12N 1/14; A01N 13/00
[52] U.S. Cl. .................... 435/254.1; 435/93.2; 435/93.5; 424/911
[58] Field of Search ................................. 435/254.1, 911; 424/93.1, 93.2, 93.5

[56] References Cited

U.S. PATENT DOCUMENTS 5,268,173  12/1993  Howell et al. ........................ 424/93 Q

OTHER PUBLICATIONS

Howell, C.R. and Stipanovic, R. D., "Mechanisms in Cotton Soreshin Biocontrol by *Trichoderma Virens*: Viridiol Production", distributed Jan. 10, 1996 at the Beltwide Cotton Prod. Res. Conference.

Howell, C.R. and Stipanovic, R.D., "The biocontrol efficacy and phytotoxicity of viridiol–deficient mutants of *Gliocladium virens*", handed out Apr. 18, 1995 at Fifth International Trichoderma/Gliocladium Workshop.

Jones, Richard W. and Hancock, Joseph G., "Conversion of viridin to viridiol by viridin–producing fungi", *Can J. Microbiol.*, vol. 33, 1987, pp. 963–966.

Howell, Charles R., and Stipanovic, Robert D., "Gliovirin, a new antibiotic from *Gliocladium virens*, and its role in the biological control of *Pythium ultimum*", *Can. J. Microbiold.*, vol. 29, Mar. 1983, pp. 321–324.

Wilhite et al., Phi/to Pathology, 84:816–21, 1994.

Ahmad et al., Can. J. Microbiol., 1988, 34(5), 694–6.

Howell et al., Can. J. Microbiol, 1983, 29(3) 321–324.

Demain et al., Manual of Industrial Microbiology and Biotechnology, 1986, ASM.

*Primary Examiner*—Irene Marx
*Attorney, Agent, or Firm*—M. Howard Silverstein; Randall E. Deck; John D. Fado

[57] ABSTRACT

A process for producing strains of *Trichoderma virens* which are deficient for production of viridiol for use as biocontrol agents is disclosed. These mutant strains are produced by treatment of viable *T. virens* with chemical or physical mutagens, preferably by irradiation with ultraviolet light. The treated fungi are then screened for production of viridiol to select for deficient strains. Following recovery, the mutant strains may be used as biocontrol agents for the control of plant diseases by application to the locus of a plant, seedling or seed to be protected. Coating seeds with the biocontrol agent prior to planting has been found to be particularly effective for the control of soilborne root or seedling diseases.

19 Claims, No Drawings

VIRIDIOL DEFICIENT MUTANT STRAINS OF THE BIOCONTROL AGENT TRICHODERMA VIRENS, PROCESS OF MAKING AND USING AS BIOCONTROL AGENT

BACKGROUND OF THE INVENTION

1. Field of the Invention

The invention relates to a biological control agent for control of fungal diseases in plants.

2. Description of the Prior Art

*Trichoderma virens* (formerly known as *Gliocladium virens*) has been recognized as a mycoparasite and antibiotic-producing antagonist of plant pathogens, and has been used as an effective biocontrol agent of several soil-borne root or seedling diseases [Aluko and Hering, 1970, Trans. Br. Mycol. Soc., 55:173–179; Beagle-Ristaino and Papavizas, 1985, Phytopathology, 75:560–564; Howell, 1982, Phytopathology, 72:496–498; Howell and Stipanovic, 1983, Can. J. Microbiol., 29:321–324; Weindling and Fawcett, 1936, Hilgardia, 10:1–16; and Wright, 1956, Plant Soil, 8:132–140]. *T. virens* produces gliotoxin and gliovirin, which are particularly effective antifungal antibiotics, as well as the antibacterial compound heptelidic acid and the antifungal compound viridin.

In addition to its use as an antifungal biocontrol agent, *T. virens* has also been employed as a mycoherbicide [Jones et al., 1988, Weed Science, 36:683–687; and Howell and Stipanovic, 1984, Phytopathology, 74:1346–1349]. Herbicidal activity has been attributed to the production of viridiol, a steroidal phytotoxin which is very toxic to the growing tip of the emerging radicle of a germinating seedling and results in necrosis of the meristematic tissue and severe stunting of the root.

Unfortunately, viridiol has not only been shown to be phytotoxic to weeds such as pigweed, but also to valuable crop plants such as cotton seedlings [Howell et al., Phytopathology, 74:1346–1349 (1984)]. Thus, the production of the phytotoxic compound viridiol may severely restrict the use of *T. virens* as a biocontrol agent for the control of plant diseases, limiting the amount of *T. virens* that can be applied to crops and/or seeds.

This problem can be partially alleviated by the addition of sterol inhibiting fungicides to the developing fungus cultures as described by Howell (U.S. Pat. No. 5,268,173, the contents of which are incorporated by reference herein). However, excessive levels of these fungicides tend to inhibit the growth of the *T. virens*, and do not prevent subsequent production of phytotoxin by the fungus around the seed after planting.

SUMMARY OF THE INVENTION

I have now discovered mutant strains of *Trichoderma (Gliocladium) virens* which are deficient for production of the phytotoxin viridiol, but retain effectiveness as biocontrol agents. These mutant strains are produced by treatment of viable *T. virens* with chemical or physical mutagens, preferably by irradiation with ultraviolet light. The treated fungi are then screened for production of viridiol to select for deficient strains. Following recovery, the mutant strains may be used as biocontrol agents for the control of plant diseases by application to the locus of a plant, seedling or seed to be protected. Coating seeds with the biocontrol agent prior to planting has been found to be particularly effective for the control of soilborne root or seedling diseases.

In accordance with this discovery, it is an object of this invention to provide a biocontrol agent for the control of plant diseases which is not phytotoxic to the plant being treated.

It is also an object of this invention to provide an improved process for producing mutant strains of *T. virens* which are deficient for the production of viridiol for use as biocontrol agents.

Other objects and advantages of this invention will become readily apparent from the ensuing description.

DETAILED DESCRIPTION OF THE INVENTION

The fungal organisms for use in this invention are novel mutant strains of *Trichoderma virens* (formerly *Gliocladium virens*). I have unexpectedly discovered that mutants of *T. virens* may be produced which are deficient in the ability to produce viridiol, but which retain the effectiveness of the parent strains as biocontrol agents against fungal diseases of plants. In brief, cells of *T. virens* are subjected to mutagenesis and then screened to select mutant strains showing no or significantly reduced production of viridiol.

The sources of *T. virens* parent strains used in this invention are not critical. The strains may be obtained from a wide variety of sources, including but not limited to naturally occurring strains from soil, plant debris, or fungus propagules, or purified isolates. Traditionally, strains of this organism have been separated into one of two broad groups, designated P and Q, based upon viridin and pigment production. Howell and Stipanovic previously found that these groups differ not only in colony pigmentation, but also in antibiotic production, with the P group producing yellow pigment and gliovirin but not gliotoxin, and the Q group producing gliotoxin but not gliovirin or the pigment (1991, Petria, 1:129–130, the contents of which are incorporated by reference herein). Owing to differences in activity of these antibiotics, it is envisioned that strains from either group may be selected for use in this invention in accordance with their efficacy against a given target disease. For example, when activity against the causative agent of root rot of white beans, i.e. *Rhizoctonia solani*, is required, Q strains are preferred. In contrast, P strains are preferred when the target pathogen is *Pythium ultimum*, the causative agent of cotton seedling disease (damping-off). When a broad spectrum of activity is desired, mixtures of one or more strains from each group may be used, enabling production of both gliotoxin and gliovirin.

Mutation of the parent strains may be induced by treatment thereof with mutagens known in the art, with a variety of conventional mutagens which are effective for inducing random mutations in the genotype being suitable for use herein. These mutagens include, but are not limited to, ultraviolet irradiation, X-ray irradiation, or chemical mutagens including base analogs such as 5-bromouracil or 2-aminopurine, deaminating agents such as nitrous acid or hydroxylamine, alkylating agents such as ethyl ethanesulfonate or nitrosoguanidine (N-methyl-N'-nitro-N-nitrosoguanidine), or acridine derivatives, or combinations of any of the above. The methodology of inducing mutations in the parent strains may be readily determined by the practitioner skilled in the art, and will of course vary with the specific mutagen selected. Conventional mutagenesis procedures which are suitable for use herein have been described, for example, by Miller (Experiments in Molecular Genetics, Cold Spring Harbor Laboratory, 1972, pp. 111–185), Esser and Kuenen (Genetics of Fungi, Springer Verlag, New York, 1967, pp. 266–294), or Davis et al. (Microbiology: Including Immunology and Molecular Genetics, Harper & Row, Hagerstown, Md., 1973, pp. 254–259), the contents of each of which are incorporated by reference herein.

In accordance with the preferred embodiment, cells of a parent strain are subjected to ultraviolet radiation to induce mutation. The wavelength and exposure time, and hence the level of mutagenesis, are not critical, and may be readily determined by the practitioner skilled in the art. However, as known to those in the art, the higher the level of mutagenesis, the higher the percentage of mutants recovered. For practical purposes, it is envisioned that the wavelength of the radiation may range between about 200 to 300 nm, although wavelengths between about 250 to 260 nm are preferred. Generally, the exposure period should be selected to kill approximately 90 to 99% of the cells, with a kill rate of about 95% being preferred. While exposure periods giving a lower kill rate may be employed, relatively low numbers of mutants may be induced. The precise exposure period for a given treatment may vary with the particular wavelength chosen, the path length of the medium containing the cells (i.e., the depth through which the light must pass) and the presence of contaminants or other UV absorbing components in the medium. Suitable exposure times for a particular wavelength may be readily determined from lethal killing curves of % killed vs. time of treatment. The temperature of the treatment also is not critical, although very high temperatures which may be lethal should be obviously avoided. Subsequent to mutagenesis, the resultant strains are cultured and screened as described below to select the specific colony or colonies which are deficient for the production of viridiol.

Mutagenic treatments may be applied to virtually any morphological form of *T. virens*, including mycelia. However, to facilitate later isolation and screening of the treated cells, the treatment is preferably applied to conidia. Following treatment, conidia may be readily cultured at such a dilution that each viable conidium gives rise to a single discrete colony, free from contamination of non-mutated cells.

In preparation for mutagenesis, the parent strains of *T. virens* may be cultivated under any conventional aerobic conditions that promote their growth. Although a variety of conventional solid and liquid culture media may be suitable for use herein, growth on solid media is preferred for ease of recovery of conidia. The skilled practitioner will recognize that culture media that are optimal for growth will vary with the strain of *T. virens* used, and may be readily determined using conventional techniques. Without being limited thereto, preferred media include conventional mycology culture media such as Czapek's agar, cornmeal agar or potato-dextrose agar, or in the alternative, any of the culture media described by Howell [Phytopathology, 1991, 81:738–741, the contents of which are incorporated by reference herein]. The fungi will grow over wide temperature and pH ranges, generally between about 15° to 33° C. and about 4.0 to 7.5, respectively, with room temperature of 25° C. and a pH of about 5.5 being preferred. Once a sufficiently heavy growth of the fungus has been obtained, usually in about 3 to 5 days, conidia may be recovered, for example, by scraping the colonies with a bladed instrument such as a spatula or scalpel. When harvested in this manner, the conidia readily separate from the hyphae, adhering to the scraping instrument. Harvested conidia may be stored in glycerol or in a dry environment, frozen or lyophilized, or they be may dispersed in a suitable carrier such as water or buffer for immediate treatment.

As mentioned hereinabove, following mutagenesis, the treated cells of *T. virens* are screened to isolate any mutant strains which are deficient for production of viridiol. Viridiol deficient strains are defined herein as those strains producing essentially no or significantly reduced levels of viridiol in comparison to their parent strain. In the preferred embodiment those strains are selected wherein production of viridiol is reduced by about 80 to 100% in comparison to the parent strains.

Screening is generally carried out by inoculating the treated cells onto a solid culture medium, incubating under conditions effective to promote growth, and identifying those colonies which are deficient for viridiol production. Although the treated cells may be inoculated onto conventional culture media, colonies of the desired mutants are indistinguishable from colonies of cells (non-mutated or mutated) which are not deficient for production of viridiol. Unfortunately, viridiol has no known antimicrobial activity, nor does it readily combine with other chemicals to form visible products at room temperature, which would enable ready detection. Consequently, all colonies must be subjected to extraction and analysis, such as by high pressure liquid chromatography (HPLC), to identify mutant strains deficient in viridiol. This process is obviously very costly and time consuming.

I have surprisingly discovered a novel screening process which allows rapid and relatively inexpensive screening and isolation of viridiol deficient mutants. In accordance with this process, the treated cells are inoculated onto a culture medium containing low levels of steroid inhibitor. Use of this culture medium adversely effects the growth of cells which are not deficient for the production of viridiol, while the growth of mutant strains which are deficient for production of this compound is not effected or is effected to a substantially lesser extent. Upon incubation on this steroid inhibitor supplemented culture medium, strains which are deficient for production of viridiol develop substantially larger colonies in terms of radial growth than non-deficient strains. Larger colonies may then be selectively subcultured and/or analyzed using conventional techniques to determine the precise level of viridiol production.

Without being bound by theory, it is believed that because sterol is necessary for growth of *T. virens*, and a significant portion of the sterol is used by the organism to produce viridiol, any viridiol deficient strains should have more sterol available to overcome the negative effects of sterol-inhibiting fungicides in the culture medium. Thus, the addition of the steroid inhibitor would exert a greater adverse effect on parent colonies than on mutants which are deficient for viridiol synthesis.

The basal nutrient medium used to prepare the screening culture medium is not critical. Any conventional culture media are suitable, including, for example, those described above for the propagation of the *T. virens* parent strains. It is anticipated that a variety of fungicidal steroid inhibitors or mixtures thereof may also be used. Without being limited thereto, inhibitors belonging to the classes of triazole and silane steroid inhibitors are preferred, with propiconazole, flusilazole, myclobutanil and triadimenol, and to a lesser extent bitertanol, penconazole, and triadimefon, being particularly preferred. The selection of other suitable steroid inhibitors may be readily determined by the practitioner skilled in the art.

The concentration of sterol inhibitor added to this basal nutrient medium should be sufficient to substantially restrict the radial growth of non-viridiol deficient and parent strains, in comparison with viridiol deficient strains. This amount, which will vary with the particular sterol inhibitor used, may be readily determined by the practitioner skilled in the art using conventional techniques. By way of example, in the preferred embodiment, addition of between about 0.2 to 0.3 μg/ml of flusilazole to a solid culture medium such as potato dextrose agar enables excellent differentiation of the viridiol deficient strains. The skilled practitioner will recognize that other concentrations may also be effective.

Once the treated cells have been inoculated onto the sterol inhibitor containing culture medium, they are incubated under conventional aerobic culture conditions which will promote growth of *T. virens*. Generally, these conditions may be the same as those described above for the propagation of the parent strains. The cultures are then examined for the presence of colonies with radial growth rates greater than that of the majority of colonies. These larger colonies, which are considered to be putative mutants deficient in viridiol production, may then be analyzed directly to confirm the precise level of viridiol production, or they may be preferably first transferred to a suitable fresh culture media and subcultured for isolation as a pure culture. The putative mutants may be subcultured onto solid or liquid culture media, although eventual subculture into liquid culture media is preferred due to ease of separation of the cellular material for confirmatory analysis.

Analysis of the above-mentioned putative mutants for quantitative determination of viridiol production may be conducted using techniques conventional in the art. The particular technique used is not critical. In the preferred embodiment, cultures of the putative mutants are analyzed using the processes described by Howell (U.S. Pat. No. 5,268,173) or in the examples hereinbelow. Briefly, after removal of solids from a culture of the putative mutants, the culture supernatants are extracted with chloroform, dried, and the resultant residues dissolved in methanol. Samples of the extracts may then be analyzed by HPLC to obtain a quantitative measurement of viridiol production. Optionally, the extracts may be analyzed for production of beneficial antibiotics, such as gliotoxin or gliovirin, and heptelidic acid. Presence of these antifungal agents provides an indication that the mutants have retained biocontrol efficacy.

Putative mutants which have been confirmed as being deficient in viridiol production may be further examined for their biocontrol efficacy and phytotoxicity. This is particularly beneficial when gliotoxin or gliovirin production has not been determined. Seeds or seedlings treated with the viridiol deficient mutants are planted in soil contaminated with a fungal pathogen such as *Rhizoctonia solani* or *Pythium ultimum*. After incubation, the seeds or seedlings are examined for evidence of disease. Viridiol deficient strains which are effective to prevent or significantly reduce the incidence or degree of disease (in comparison to untreated controls) are retained for subsequent use as biocontrol agents. Optionally, seeds or seedlings may also be treated with the viridiol deficient strains and incubated in pathogen-free soil to confirm a reduction in phytotoxicity (in comparison to parent strains). Details of suitable biocontrol and phytotoxicity assays are described in Howell (U.S. Pat. No. 5,268,173) and in the Examples.

Strains confirmed as deficient for viridiol production are preferably examined for genetic stability to screen out revertants. A strain is considered to be genetically stable for the purpose of this invention if the strain retains its deficiency in viridiol production after continued cultivation for approximately one to two weeks. Because some revertants may suffer a reduction in biocontrol efficacy, the mutant strains are also preferably re-evaluated for biocontrol efficacy at the same time.

Mutant strains which are viridiol deficient, retain biocontrol efficacy, and are genetically stable, are retained for use herein. To produce large amounts suitable for commercial use, the fungi may be cultivated by any conventional means as described above. Under cultivation conditions, the subject fungi will produce gliotoxin or gliovirin concurrently with growth, and the fermentation should be continued for sufficient time to produce maximum levels of cells and antibiotics. Effective conditions for the fermentation, including pH, temperature and time, may be readily determined by the practitioner in the art. Once again, a variety of solid or liquid culture media are also suitable for use in the invention. The skilled practitioner will recognize that culture media that are optimal for growth and production of gliovirin and gliotoxin will vary with the strain of *T. virens* used, and may be readily determined using conventional techniques. Without being limited thereto, preferred media include millet, rice hull, wheat, wheat bran, sorghum, soybean, cotton, rice, oats, or supplemented peat moss as described by Howell [Phytopathology, 1991, ibid]. Of these, millet or rice hull media are particularly preferred, with a plurality of strains of *T. virens* exhibiting greater biocontrol activity when grown thereon.

Following completion of the fermentation, the resultant culture of *T. virens* containing gliovirin or gliotoxin may be recovered for use as a biocontrol agent. As a practical matter, it is envisioned that commercial formulations of the subject biocontrol agent would be prepared directly from the culture, thereby obviating the need for any purification steps. While liquid cultures could be applied directly upon or to the locus of the plant, seedling or seed to be treated, in the preferred embodiment, the water is removed from liquid cultures to partial or substantial dryness, and the dried culture broken up or ground into small particles using techniques conventional in the art. Without being limited thereto, suitable water removal techniques include air drying, evaporation or filtration.

In a particularly preferred embodiment, the granules are contacted with a sticking agent or adherent as are known in the art to facilitate adherence of the granular biocontrol agent to a target seedling or seed to be treated. Suitable sticking agents may be readily determined by the skilled practitioner and include but are not limited to latex (RHOPLEX B-15, Rohm and Haas, Philadelphia, Pa.), sugars such as sucrose, glucose, fructose, mannose, α-methyl glucoside or corn syrup (as described by Shasha and McGuire, U.S. Pat. No. 5,061,697, issued Oct. 29, 1991, the contents of which are incorporated by reference herein), alginate, methylcellulose, and OPADRY (Colorcon, Inc., Westpoint, Pa.). The sticking agent may be applied onto either the granules or seed prior to use. When seeds are being treated, they may be precoated with biocontrol agent prior to sale by the seed supplier, or they may be coated in the field.

In an alternative embodiment, controlled release of the biocontrol agent may be accomplished by encapsulation within an inert carrier using conventional techniques. Suitable carriers of this type include but are not limited to alginate gels, wheat-gluten matrices, starch matrices, or synthetic polymers as are known in the art. Preferred alternative carriers and methods for immobilizing nematodes are described, for example, in Walker et al. or Connick (U.S. Pat. Nos. 4,767,441 and 4,401,456, respectively, disclosing alginate gels), Doane et al. (U.S. Pat. No. 4,911,952 disclosing starch matrices), and Trimnell et al. (U.S. Pat. No. 4,439,488 disclosing polyhydroxy polymer borates), the contents of each of which are herein incorporated by reference.

Besides the culture, other additives and adjuncts may be formulated into the subject biocontrol composition. Examples of these include additional nutrients, inert fillers, UV protectants such as Congo-red, folic acid, paraminobenzoic acid or azobenzene, fertilizers, or pesticides. Particularly preferred for inclusion are fungicides. Without being limited thereto, suitable fungicides include carboxin, pentachloronitrobenzene or metalaxyl, which are commonly used as cottonseed treatments to control seedling diseases. As disclosed by Howell (U.S. Pat. No. 5,268,173), when reduced concentrations of metalaxyl were used in combination with the biocontrol agent as a seed coating, a synergistic effect was observed.

To be effective, the biocontrol agent must be applied to the locus of, or in the vicinity of, the plant, seedling or seed to be protected. In one preferred embodiment, the biocontrol agent is applied as a seed treatment coated onto the seeds, thus assuring the presence and production of antibiotics in the vicinity of the growing plant. In another preferred embodiment, the biocontrol agent may be applied into the furrows together with the seed during planting. Ideally, particulate biocontrol agent (with or without sticking agent) will be admixed with the seeds in the planter hopper to ensure its application into the furrow in close proximity to the seed. The practitioner skilled in the art will recognize that while the biocontrol agent could be separately applied to the soil or, in the case of greenhouse plants, added to potting mix of plants grown in greenhouse conditions [Lumsden et al., 1990, Phytopathology, 79:361–366; and Smith et al., 1990, Phytopathology, 80:880–885], such techniques require relatively large volumes of the biocontrol agent which are impractical in the field.

Depending upon the species of the target disease, the subject biocontrol agent acts to control the causative fungal pathogen by death inducement or inhibiting growth or infectivity, all of which mechanisms are evidenced by a decrease in the incidence or severity of the plant or seedling disease associated with the pathogen. The biocontrol agent of this invention is administered in an amount effective to control a target disease as determined by routine testing. An "effective amount" of biocontrol agent is defined herein as those quantities of agent that will result in a significant decrease in the incidence or severity of the plant or seedling disease as compared to an untreated control. The actual effective amount will vary with the disease and causative fungal pathogen, the strain of *T. virens*, the formulation and method of treatment, and environmental conditions, and may be readily determined by the practitioner skilled in the art. When applied as a coating on cotton seeds, suitable amounts of biocontrol agent range from, but are not limited to, greater than about 0.5–1 g of dried particulate biocontrol agent per 100 cottonseeds.

The biocontrol agent encompassed herein is effective in controlling plant and seedling diseases of a plurality of plants. Without being limited thereto, the agent may be applied to any agronomically important plant or its seedling or seed, especially seeds of cotton, soybeans, beans, citrus, apples and zinnia.

Although the screening process of this invention has been described for use in identifying artificially induced mutants, it is understood that the same process may be used to screen and isolate naturally occurring mutant or new strains of *T. virens* for viridiol deficiency.

The following examples are intended only to further illustrate the invention and are not intended to limit the scope of the invention which is defined by the claims.

EXAMPLE 1

Isolation and Characterization of *T. virens* strains

The parent strains of *T. virens* used in this study were pure isolates from soil, plant debris, or fungus propagules and stored as conidia in 50% aqueous glycerol at −75° C. to maintain genetic purity. Strains used for experimentation were maintained on potato dextrose agar (PDA). The strains used in this study were all from the Q group, indicating that they produce the antibiotic gliotoxin as a major metabolite.

Mutation and Detection Techniques

Mutation of these strains was accomplished by irradiating 10 ml of a $2\times10^6$ conidia suspension of the fungus, while stirring, with 600 W/cm$^2$ of 254 nm UV light for 55 seconds. Serial Dilutions were made of the irradiated conidia to give $5\times10^2$ conidia per ml, and 0.1 ml aliquots were spread on the surface of agar screening media.

The growth medium for screening for mutant colonies consisted of PDA containing 0.25 $\mu$g/ml of the sterol-inhibiting triazole fungicide flusilazole (NUSTAR, Dupont). After 4 days at 25° C., the agar plates inoculated irradiated conidia were observed for the presence of colonies with radial growth rates greater than that of the majority of colonies. Those colonies showing this characteristic were transferred to fresh PDA.

Analysis of Metabolites from Putative Mutants

PDA plugs (0.7 mm) from actively growing cultures of putative mutants were transferred to liquid cultures (50 ml) consisting of 5% ground millet, 1% ground peat moss, and water adjusted to pH 4.0. The cultures were shake incubated for 4 days at 25° C., then the cultures were centrifuged at 16,000×g for 10 minutes. The supernatant fluids were decanted from the pellets and saved. The pellets were spread in petri dishes and dried at room temperature under a hood for 24 hours. They were then ground into fine granules and stored at 5° C. until used in bioassays.

The culture supernatant fluids were extracted with equal volumes of chloroform, and the chloroform extracts were taken to dryness in vacuo. The residues were each dissolved in 1 ml aliquots of methanol. Samples (30 $\mu$l) of the extracts were spotted on silica gel 4GF and developed with chloroform:acetone (70:30). Authentic viridiol was developed on the plates as a control, and the extracts were observed for the presence of viridiol as evidenced by the presence of a dark absorbing spot under 254 nm UV light at the same Rf as authentic viridiol controls. Those extracts showing an absence or reduced presence of viridiol were then separated with high pressure liquid chromatography (HPLC), using a Hewlett Packard 1090 liquid chromatogram equipped with a diode array detector. The reverse phase column was developed with an acetonitrile and dilute phosphoric acid mixture. This was to obtain quantitative data on the concentration of viridiol and other metabolites in the culture medium.

Possible revertants were screened for by repeating the above culture and extraction process after mutants had been subcultured on agar media for several weeks.

Biocontrol Efficacy and Phytotoxicity

The air dried granular preparation of parent and viridiol deficient mutant strains stored at 5° C. were coated on cotton seed with a latex sticker and planted in flats containing field soil contaminated with *Rhizoctonia solani*. The flats were incubated in a growth chamber at 25° C. and with a 12 hour photoperiod for 10 days, then the numbers of emerged and healthy seedlings were counted. The treatments were replicated and randomized within the flats.

Large test tubes containing moist sterile field soil were planted with cotton seed treated with concentrations of air dried preparations of parent and mutant strains 10-fold that applied to cotton seed for disease control tests. After 10 days incubation in growth chambers at 25° C. and a 12 hour photoperiod, the resulting seedlings were washed from the tubes and examined for symptoms of phytotoxicity.

Results

Of the conidia irradiated and plated on the agar screening medium, approximately 1% showed increased radial growth in the presence of NUSTAR and were transferred to fresh media for confirmatory testing. Growth of parent strains on this medium resulted in button-like colonies, whereas the mutant strains showed diffuse and spreading growth. However, a small number of the mutant colonies, approximately 2–3%, showed morphological deformities (very poorly formed conidia) that rendered them unsuitable for further evaluation. Of those mutant colonies that were inoculated into liquid culture media, approximately 20% were confirmed to be deficient for viridiol production, but maintained production of gliotoxin, when the extracts were chromatographed. The HPLC profiles for the extracts were below detectable levels.

Both parent and viridiol deficient mutant strains showed similar amounts of the antibiotics gliotoxin, viridin, and heptelidic acid. The mutant strains also retained a capacity to parasitize the pathogen *R. solani* that was nearly equivalent to that of the parent strains. When these strains were reevaluated by growing them in larger amounts for longer periods of time, some of the mutant strains reverted to viridiol production. Other strains that did not revert to viridiol production were found to have reduced biocontrol activity when assayed against *R. solani* in growth chamber tests. However, some of the mutant strains that were deficient for viridiol production showed biocontrol efficacy equal to that of the parents.

Harvest and visual examination of seedlings resulting from seed treated with 10-fold concentrations of biocontrol preparations from the parent and mutant strains and planted in sterile soil showed the following: seedlings from seed treated with parent strains showed extreme stunting of the emerging radicle (1 cm or less) and necrosis of the growing tip; seedlings from seed treated with mutant strains showed well developed tap roots with good secondary root formation; development of root systems from mutant treated seed was slightly retarded when compared to the nontreated control, but no more than that seen with other commonly used fungicides.

Three stable mutant strains (designated TV-111, TV-115 and TV-109) of *T. virens*, derived from two parent strains of *T. virens* (designated TV-11 and TV-20), which exhibited optimal characteristics were retained. All three mutant strains were deficient for viridiol production and showed good biocontrol efficacy and little or no seedling phytotoxicity. The results of the HPLC analysis for these three strains and their parents is shown in Table 1. The results of the biocontrol efficacy and phytotoxicity studies for these same strains is shown in Table 2.

The three mutant strains, TV-111, TV-115, and TV-109, possess microscopic and colonial morphologies characteristic of *Trichoderma virens*. The teleomorph of this species is *Hypocrea sublutea*. Upon microscopic examination, all three strains are hyphomycetes that bear single celled green conidia in water droplets at the tip of densely penicillate conidiophores. They also produce thick-walled chlamydospores in the culture medium.

It is understood that the foregoing detailed description is given merely by way of illustration and that modifications and variations may be made therein without departing from the spirit and scope of the invention.

TABLE 1

Secondary metabolites produced by parent and mutant strains of *Trichoderma virens* in liquid culture

| Strain | VDL | GLT | VDN | HPA |
|---|---|---|---|---|
| TV-11 (P) | 1000 | 351 | 10 | 83 |
| TV-111 (M) | ND | 336 | ND | 76 |
| TV-115 (M) | ND | 382 | ND | 92 |
| TV-20 (P) | 921 | 242 | 5 | 83 |
| TV-109 (M) | 23 | 294 | ND | 58 |

VDL = viridiol; GLT = gliotoxin; VDN = viridin; HPA = heptelidic acid; (P) = parent strain; (M) = mutant strain; ND = not detectable.
Numerical data are expressed in μg/ml.

TABLE 2

Biocontrol efficacy of parent and viridiol-deficient mutants of *Trichoderma virens* against *Rhizoctonia solani* incited cotton seedling disease

| Strain | Viridiol | % seedling survival |
|---|---|---|
| TV-11 | + | 63 |
| TV-111 | − | 73 |
| TV-115 | − | 70 |
| TV-20 | + | 67 |
| TV-109 | − | 62 |
| NT control | | 10 |

We claim:

1. A process for producing a strain of *Trichoderma virens* deficient in viridiol production for use as a biocontrol agent against fungal diseases in plants comprising:
   (a) exposing cells of a parent strain of *Trichoderma virens* to a mutagen effective for inducing mutations in the genotype of said cells;
   (b) screening the mutagen exposed cells from (a) to select mutant strains which produce essentially no or significantly reduced levels of viridiol in comparison to said parent strain, wherein said screening comprises culturing said mutagen exposed cells from (a) on a culture medium containing an amount of a fungicidal steroid inhibitor effective for inhibiting growth of said parent strain of *Trichoderma virens* without substantially inhibiting growth of said mutant strains which are deficient for production of viridiol, and isolating colonies from said culture medium which exhibit greater radial growth rates than non-viridiol deficient strains of *Trichoderma virens*; and
   (c) further screening said mutant strains from (b) to:
      (i) select for those strains which produce at least one antifungal compound selected from the group consisting of gliotoxin, gliovirin, viridin, and heptelidic acid; or
      (ii) select for those strains which exhibit efficacy as biocontrol agents against fungal diseases in plants.

2. The process as described in claim 1 wherein said parent strain of *Trichoderma virens* is a Q strain.

3. The process as described in claim 1 wherein said mutagen is selected from the group consisting of ultraviolet radiation, x-ray radiation, and chemical mutagens.

4. The process as described in claim 3 wherein said mutagen is ultraviolet radiation.

5. The process as described in claim 1 wherein said cells of *Trichoderma virens* are exposed to said mutagen for a period of time sufficient to kill between about 90 to 99% of said cells.

6. The process as described in claim 1 wherein said steroid inhibitor is selected from the group consisting of triazoles, silanes and mixtures thereof.

7. The process as described in claim 1 wherein said steroid inhibitor is selected from the group consisting of propiconazole, flusilazole, triadimenol, myclobutanil and mixtures thereof.

8. The process as described in claim 1 wherein the concentration of said steroid inhibitor in said culture medium is between about 0.2 to about 0.3 µg/ml.

9. The process as described in claim 1 further comprising determining the level of viridiol produced by the isolated colonies.

10. The process as described in claim 1 wherein said mutagen exposed cells from (a) are screened to select mutant strains wherein the production of viridiol is reduced by at least about 80% in comparison to said parent strain.

11. The process as described in claim 1 wherein said further screening of (c) comprises screening said mutant strains from (b) to select for those strains which are effective as biocontrol agents against Rhizoctonia or Pythium species.

12. A mutant strain of *Trichoderma virens* deficient for the production of viridiol which is produced by the process of claim 1, and which is effective as a biocontrol agent against fungal diseases in plants.

13. A mutant strain of *Trichoderma virens* deficient for the production of viridiol which is produced by the process of claim 10.

14. The mutant strain of claim 12 which is selected from the group consisting of *Trichoderma virens* TV-111, *Trichoderma virens* TV-115, and *Trichoderma virens* TV-109.

15. A method for controlling plant disease comprising applying the mutant strain of *Trichoderma virens* of claim 12 to the locus of a plant, seedling or seed.

16. The method as described in claim 15 wherein the step of applying comprises applying said mutant strain onto a seed.

17. The method as described in claim 16 wherein said seed is selected from the group consisting of cottonseeds, soybeans, beans, citrus seeds, apple seeds, and seeds of zinnia.

18. The mutant strain of claim 12 which is effective as a biocontrol agent against Rhizoctonia or Pythium species.

19. The mutant strain of claim 18 which is effective as a biocontrol agent against *Rhizoctonia solani* or *Pythium ultimum*.

* * * * *